(12) United States Patent
Addison et al.

(10) Patent No.: US 12,727,909 B2
(45) Date of Patent: Sep. 8, 2026

(54) INTRODUCER CANNULA HAVING A PLEURAL ACCESS LINER FOR USE IN CROSSING PLEURAL LAYERS

(71) Applicant: Bard Peripheral Vascular, Inc., Franklin Lakes, NJ (US)

(72) Inventors: Jordan Addison, Gilbert, AZ (US); Heather Storm, Phoenix, AZ (US)

(73) Assignee: Bard Peripheral Vascular, Inc., Franklin Lakes, NJ (US)

( * ) Notice: Subject to any disclaimer, the term of this patent is extended or adjusted under 35 U.S.C. 154(b) by 1126 days.

(21) Appl. No.: 17/784,369

(22) PCT Filed: Dec. 19, 2019

(86) PCT No.: PCT/US2019/067519
§ 371 (c)(1),
(2) Date: Jun. 10, 2022

(87) PCT Pub. No.: WO2021/126213
PCT Pub. Date: Jun. 24, 2021

(65) Prior Publication Data

US 2023/0046435 A1 Feb. 16, 2023

(51) Int. Cl.
*A61B 17/34* (2006.01)
*A61B 17/00* (2006.01)

(52) U.S. Cl.
CPC .... *A61B 17/34* (2013.01); *A61B 2017/00004* (2013.01); *A61B 17/3421* (2013.01)

(58) Field of Classification Search
CPC ................ A61B 17/34; A61B 17/3421; A61B 2017/00004; A61B 17/3474;
(Continued)

(56) References Cited

U.S. PATENT DOCUMENTS 4,838,280 A 6/1989 Haaga
5,169,387 A 12/1992 Kronner
(Continued)

FOREIGN PATENT DOCUMENTS

CN 106562815 A 4/2017
CN 207804345 U 9/2018
(Continued)

OTHER PUBLICATIONS

International Search Report and Written Opinion dated Jun. 16, 2020, in International Application No. PCT/US2019/067519.
(Continued)

*Primary Examiner* — Jason E Flick
(74) *Attorney, Agent, or Firm* — Dinsmore & Shohl LLP

(57) ABSTRACT

An introducer cannula for use in crossing pleural layers includes an elongate tubular member and a pleural access liner. The elongate tubular member has a proximal end, a distal end, and a side wall that longitudinally extends between the proximal end and the distal end. The side wall has an outer surface and an inner surface, wherein the inner surface defines a lumen. The pleural access liner is made of a swellable and bioabsorbable material that swells when hydrated. The pleural access liner has a shape of an elongate tube and the pleural access liner has an elongate opening that surrounds an outer surface portion of the outer surface of the elongate tubular member.

20 Claims, 5 Drawing Sheets

(58) Field of Classification Search
CPC ...... A61B 17/3415; A61B 2017/00942; A61B 2017/3419; A61B 17/0057; A61B 2017/00654; A61B 2017/00637; A61B 2017/00898; A61B 2017/00601; A61M 29/02; A61M 2202/064; A61M 2210/101
See application file for complete search history.

(56) References Cited

U.S. PATENT DOCUMENTS 5,176,649 A 1/1993 Wakabayashi
5,222,974 A 6/1993 Kensey
6,270,484 B1 8/2001 Yoon
6,790,185 B1 9/2004 Fisher et al.
7,022,088 B2 4/2006 Keast et al.
7,635,341 B2 12/2009 Doorschodt
7,790,192 B2 9/2010 Sawhney et al.
8,231,581 B2 7/2012 Tanaka
8,273,051 B2 9/2012 Tanaka et al.
8,795,241 B2 8/2014 O'Connell et al.
9,028,523 B2 5/2015 Hashiba et al.
9,125,639 B2 * 9/2015 Mathis .............. A61M 25/0147
9,307,960 B2 4/2016 Keast et al.
9,693,854 B2 7/2017 Clark et al.
10,117,765 B2 11/2018 Norris et al.
10,149,665 B2 12/2018 Eckerline et al.
10,179,008 B2 1/2019 Sauer
2003/0050664 A1 3/2003 Solem
2003/0097079 A1 5/2003 Garcia
2003/0109899 A1 6/2003 Fisher
2007/0066990 A1 3/2007 Marsella et al.
2008/0058728 A1 * 3/2008 Soltz .................. A61B 17/3417
604/174
2008/0281295 A1 11/2008 Chang
2010/0274280 A1 10/2010 Sawhney
2010/0286483 A1 11/2010 Bettuchi et al.
2012/0179102 A1 7/2012 Blanchard et al.
2012/0289862 A1 11/2012 Shariati
2012/0290001 A1 11/2012 Uchida
2015/0201963 A1 7/2015 Snow
2016/0120528 A1 5/2016 Abtin
2016/0120585 A1 5/2016 Poulsen
2016/0296218 A1 10/2016 Uchida
2017/0000361 A1 * 1/2017 Meyering ........... A61M 39/223
2017/0079519 A1 3/2017 Sung et al.
2018/0279868 A1 10/2018 Sczaniecka et al.
2019/0022333 A1 1/2019 Baillargeon et al.
2022/0280142 A1 9/2022 Addison et al.

FOREIGN PATENT DOCUMENTS

CN 107174319 B 2/2024
JP 2002518121 A 6/2002
JP 2005511186 A 4/2005
JP 2018069096 A 5/2018
JP 2018520761 A 8/2018
KR 20140035972 A 3/2014
KR 20220079537 A 6/2022
WO 9966834 A1 12/1999
WO 2003049598 A2 6/2003
WO 2017004268 A1 1/2017
WO 2019138019 A2 7/2019

OTHER PUBLICATIONS

Office Action dated Mar. 8, 2024 pertaining to CN 201980103282.9, Jun. 17, 2022.

Notice of Allowance dated Sep. 10, 2024 pertaining to Korean application 10-2022-7024142 filed Jul. 13, 2022.

CN Office Action dated Aug. 31, 2024 pertaining to CN 201980103282.9 filed Jun. 17, 2022.

* cited by examiner

INTRODUCER CANNULA HAVING A PLEURAL ACCESS LINER FOR USE IN CROSSING PLEURAL LAYERS

CROSS-REFERENCE TO RELATED APPLICATIONS

This application is a U.S. National Phase of International Application No. PCT/US2019/067519, entitled "Introducer Cannula Having a Pleural Access Liner for Use in Crossing Pleural Layers" and filed Dec. 19, 2019, which is incorporated herein by reference in its entirety.

TECHNICAL FIELD

The present invention relates to a lung access procedure, such as a lung biopsy, and, more particularly, to an introducer cannula having a pleural access liner for use in crossing pleural layers.

BACKGROUND ART

Pneumothorax is a problematic complication of the lung biopsy procedure where air or fluid is allowed to pass into the pleural space as a result of the puncture of the parietal pleura and visceral pleura. Pneumothorax and, more so, pneumothorax requiring chest tube placement, are significant concerns for clinicians performing, and patients undergoing, percutaneous lung biopsies. The incidence of pneumothorax in patients undergoing percutaneous lung biopsy has been reported to be anywhere from 9-54%, with an average of around 15%. On average, 6.6% of all percutaneous lung biopsies result in pneumothorax requiring a chest tube to be placed, which results in an average hospital stay of 2.7 days.

Factors that increase the risk of pneumothorax include increased patient age, obstructive lung disease, increased depth of a lesion, multiple pleural passes, increased time that an access needle lies across the pleura, and traversal of a fissure. Pneumothorax may occur during or immediately after the procedure, which is why typically a CT scan of the region is performed following removal of the needle. Other, less common, complications of percutaneous lung biopsy include hemoptysis (coughing up blood), hemothorax (a type of pleural effusion in which blood accumulates in the pleural cavity), infection, and air embolism.

What is needed in the art is an introducer cannula having a pleural access liner for use in crossing pleural layers, which aids in the prevention of pneumothorax.

SUMMARY OF INVENTION

The present invention provides an introducer cannula having a pleural access liner for use in crossing pleural layers, which aids in the prevention of pneumothorax.

The invention, in one form, is directed to an introducer cannula for use in crossing pleural layers, which includes an elongate tubular member and a pleural access liner. The elongate tubular member has a proximal end, a distal end, and a side wall that longitudinally extends between the proximal end and the distal end. The side wall has an outer surface and an inner surface, wherein the inner surface defines a lumen. The pleural access liner is made of a swellable and bioabsorbable material that swells when hydrated. The pleural access liner has a shape of an elongate tube and the pleural access liner has an elongate opening that surrounds an outer surface portion of the outer surface of the elongate tubular member.

The invention, in another form, is directed to an introducer cannula for use in crossing pleural layers. The introducer cannula includes an elongate tubular member and a bioabsorbable member. The elongate tubular member has a proximal end, a distal end, and a side wall that longitudinally extends between the proximal end and the distal end. The side wall has an inner surface that defines a lumen. The side wall has a first outer surface portion having a first diameter and a second outer surface portion having a second diameter that is less than the first diameter. The second outer surface portion of the side wall defines an elongate exterior recess of the side wall that extends around an entirety of the elongate tubular member. The bioabsorbable member is positioned in the elongate exterior recess of the side wall of the tubular member. The bioabsorbable material configured to swell upon contact with a fluid.

An advantage of the present invention is that the pleural access liner facilitates access across pleura layers to aid in preventing pneumothorax before, or coincident with, and after the performing of a lung biopsy.

Another advantage of the present invention is that the pleural access liner is made of a swellable and bioabsorbable material that is resorbed by the patient's body over time as the tissue heals to close the biopsy access opening.

BRIEF DESCRIPTION OF DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplifications set out herein illustrate at least one embodiment of the invention, and such exemplifications are not to be construed as limiting the scope of the invention in any manner.

DESCRIPTION OF EMBODIMENTS

Figures 1, 2:
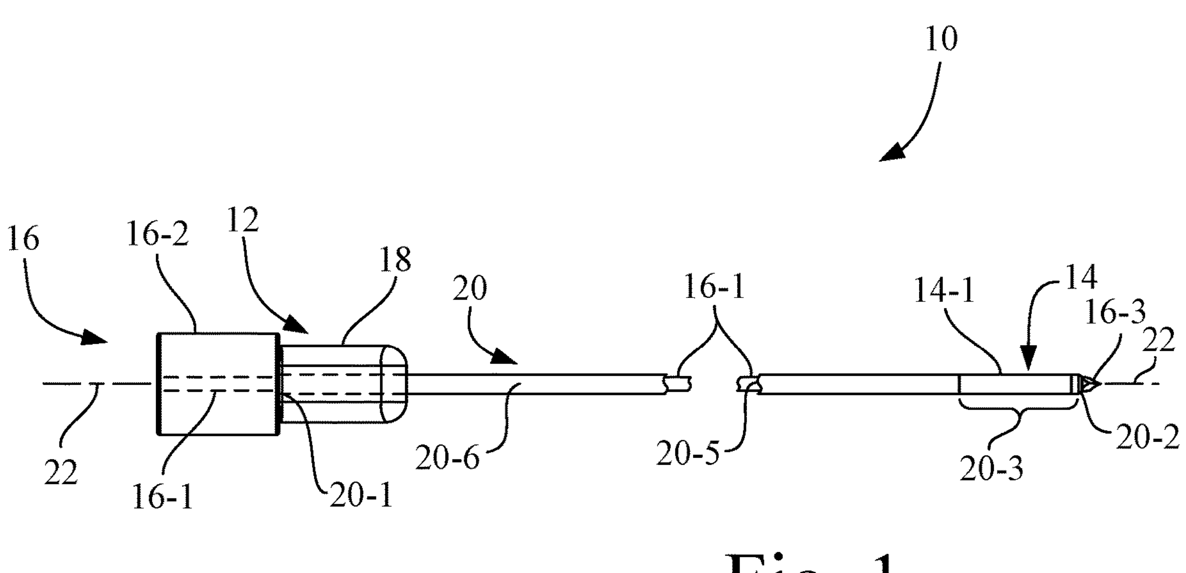
FIG. 1 is a side view of a pleural layers crossing system that includes an introducer cannula that carries a pleural access liner, coaxial with a stylet assembly, with a portion broken away to expose a part of the stylet.
FIG. 2 is an enlarged side view of a distal portion of the pleural layers crossing system of FIG. 1.

Referring now to the drawings, and more particularly to FIG. 1-4, there is shown a pleural layers crossing system 10, which includes an introducer cannula 12 having a pleural access liner 14 for use in crossing pleural layers in a lung access procedure, and a stylet assembly 16. Introducer cannula 12 and stylet assembly 16 are arranged along a longitudinal axis 22, such that introducer cannula 12 and stylet assembly 16 are coaxial.

Stylet assembly 16 includes a stylet 16-1 and a stylet handle 16-2. Stylet 16-1 has a piercing tip 16-3. Stylet handle 16-2 is fixedly connected to a proximal end portion of stylet 16-1. The term "fixedly connected" means a coupling between two or more components wherein the respective components are not readily separated from each other. For example, the fixed connection of stylet handle 16-2 to stylet 16-1 may be achieved, for example, by adhesive, weld, press fit, or screw connection.

Introducer cannula 12 includes a handle body 18 and an elongate tubular member 20. Elongate tubular member 20 has a proximal end 20-1, a distal end 20-2, a distal end portion 20-3, a lumen 20-4, and a side wall 20-5. Side wall 20-5 longitudinally extends between proximal end 20-1 and distal end 20-2, e.g., along an entire length of elongate tubular member 20. Side wall 20-5 has an outer surface 20-6 and an inner surface 20-7 that surrounds and defines lumen 20-4.

Handle body 18 is fixedly connected to elongate tubular member 20, e.g., at a location distal to proximal end 20-1, wherein lumen 20-4 passes though handle body 18. In other words, lumen 20-4 extends through handle body 18, and extends from proximal end 20-1 of elongate tubular member 20 to distal end 20-2 of elongate tubular member 20, e.g., along an entire length of elongate tubular member 20.

Figures 3, 4:
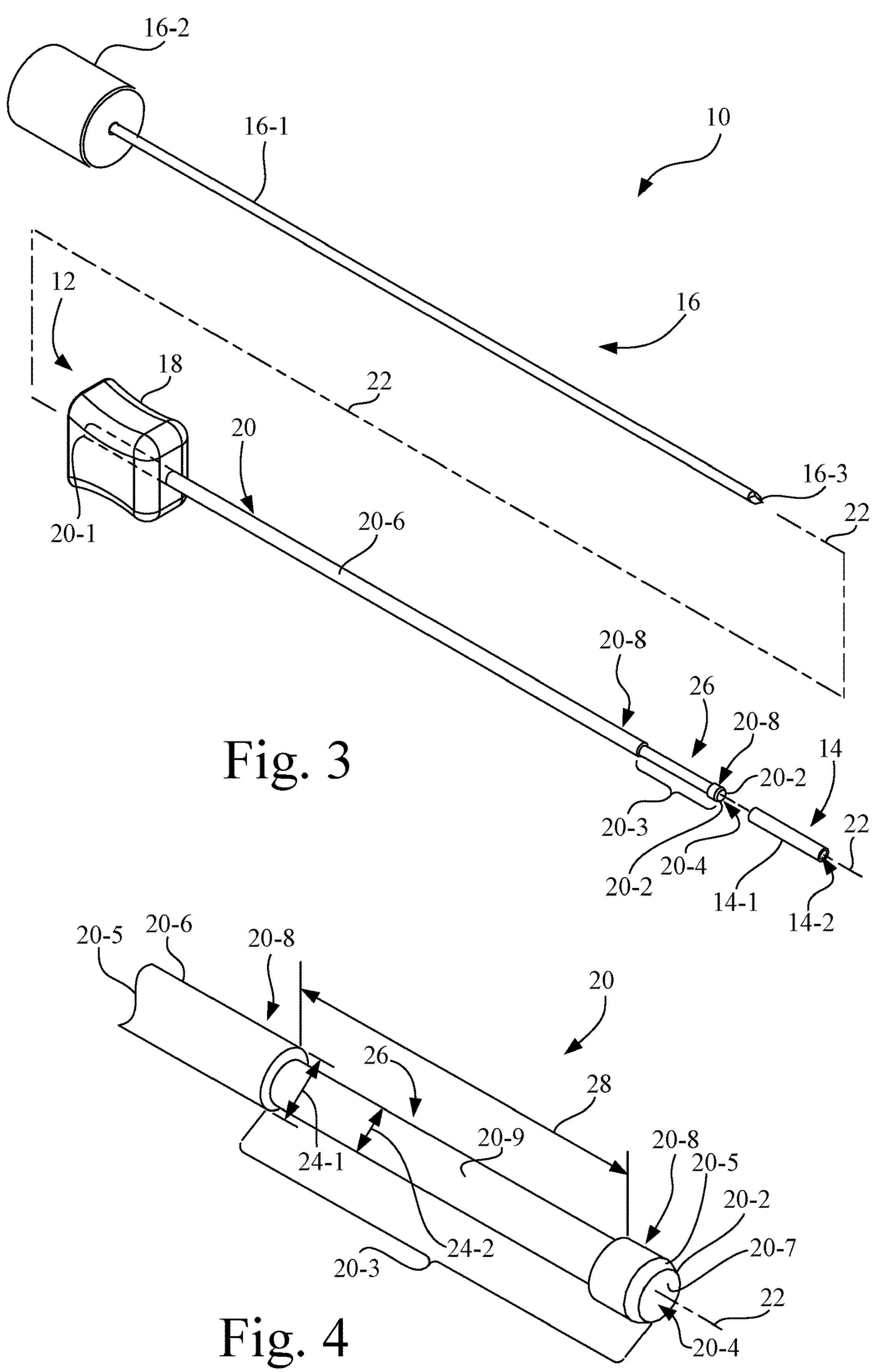
FIG. 3 is an exploded perspective view of the pleural layers crossing system of FIG. 1.
FIG. 4 is an enlarged perspective view of a distal portion of the introducer cannula shown in FIG. 3.

In the present embodiment, with particular reference to FIG. 4, outer surface 20-6 of side wall 20-5 of elongate tubular member 20 has a first outer surface portion 20-8 having a first diameter 24-1 and a second outer surface portion 20-9 having a second diameter 24-2 that is less than the first diameter 24-1, wherein the second outer surface portion 20-9 of the side wall 20-5 defines an elongate exterior recess 26 in side wall 20-5 that extends around elongate tubular member 20. In the present embodiment, elongate exterior recess 26 of the side wall 20-5 extends around an entirety of elongate tubular member 20, and has a length 28. The length 28 of elongate exterior recess 26 may be completely, or alternatively partially, longitudinally filled with pleural access liner 14. In some implementations, for example, the length 28 of elongate exterior recess 26 may be in a range of 2 to 5 centimeters.

Figure 5:
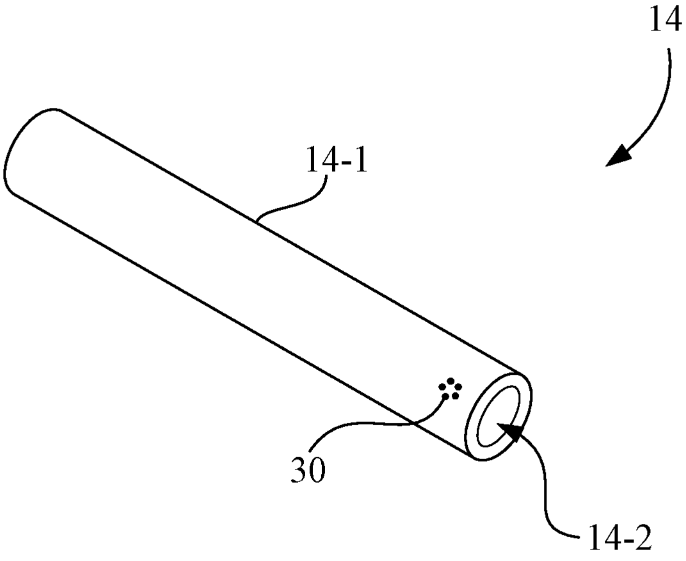
FIG. 5 is an enlarged perspective view of a pleural access liner shown in FIG. 3, with the pleural access liner in the dehydrated state.
Figure 6:
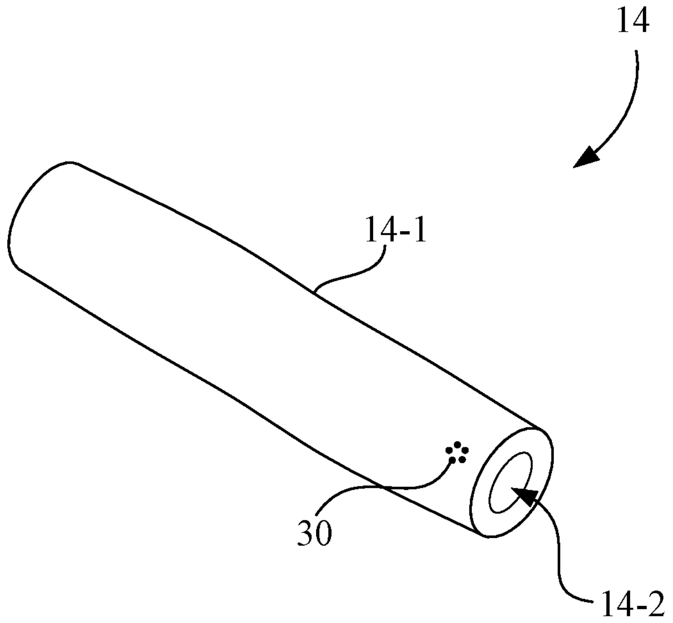
FIG. 6 is an enlarged perspective view of a pleural access liner shown in FIGS. 3 and 5, depicting the pleural access liner in the hydrated (swelled) state.

Referring also to FIGS. 5 and 6, in the present embodiment, pleural access liner 14 is a bioabsorbable member that is initially in a dehydrated state (see FIG. 5), and which is configured to hydrate and swell (see FIG. 6) upon contact with a fluid, e.g., upon contact with human bodily fluids during a lung access procedure. Referring again also to FIGS. 1-4, pleural access liner 14 may be configured as a swellable and bioabsorbable elongate cylindrical layer that is coupled to outer surface 20-6 of elongate tubular member 20, wherein the coupling of pleural access liner 14 to outer surface 20-6 of elongate tubular member 20 may be a friction fit.

In the present embodiment, with particular reference to FIGS. 5 and 6, pleural access liner 14 has a shape, e.g., a cylindrical shape, and includes an elongate tube 14-1 having an elongate opening 14-2. Elongate opening 14-2, i.e., an elongate volume, is sized and shaped, e.g., having a circular cross-section, to surround outer surface 20-6 of elongate tubular member 20 in a friction fit. More particularly, referring again also to FIGS. 1-4, in the present embodiment elongate opening 14-2 is sized and shaped to surround second outer surface portion 20-9 at elongate exterior recess 26 of elongate tubular member 20, such that pleural access liner 14 (a bioabsorbable member) resides in and radially surrounds elongate exterior recess 26 of side wall 20-5 of elongate tubular member 20. For example, pleural access liner 14, as a bioabsorbable member, may radially extend around an entirety of elongate exterior recess 26 of the side wall 20-5 of elongate tubular member 20, and may longitudinally extend along an entirety of the length 28 of elongate exterior recess 26.

Referring to FIG. 1, for example, when pleural access liner 14 is in the non-deployed (e.g. dehydrated) state, e.g., prior to insertion into a patient, pleural access liner 14 is initially a dehydrated bioabsorbable material that radially extends around, e.g., is slipped over, outer surface 20-6 of elongate tubular member 20, so as to be carried by elongate tubular member 20 for deployment. In an initial dehydrated state, a diameter of pleural access liner 14 may be substantially equal to the first diameter 24-1 of first outer surface portion 20-8 of elongate tubular member 20 of introducer cannula 12. Pleural access liner 14 may be made of at least one of collagen, silk fibroin, polyethylene glycol, hydroxypropyl methylcellulose, dehydrated gelatin, and starch. Accordingly, in some embodiments, pleural access liner 14 may be made of a polysaccharide.

In the present embodiment, for example, elongate tube 14-1 of pleural access liner 14 may be pre-formed to include elongate opening 14-2, and may be made of a foam material. During assembly, elongate tubular member 20 is inserted through elongate opening 14-2 such that elongate tube 14-1 is in friction contact with outer surface 20-6 of elongate tubular member 20, and more particularly, is in friction contact with second outer surface portion 20-9 in elongate exterior recess 26 of elongate tubular member 20. The foam material may be made of, or made to include, at least one of collagen, silk fibroin, polyethylene glycol, hydroxypropyl methylcellulose, dehydrated gelatin, and starch (or other polysaccharide), which swells when hydrated. In some embodiments, the pre-formed elongate tube 14-1 forming pleural access liner 14 may be, for example, a tube of woven or electrospun fibers.

In an alternative embodiment, for example, pleural access liner 14 may be a powder coating coupled to, e.g., adhered to, outer surface 20-6 of elongate tubular member 20 to form an elongate swellable cylindrical layer around outer surface 20-6 of elongate tubular member 20. For example, the powder coating forming pleural access liner 14 may be coupled to second outer surface portion 20-9 at elongate exterior recess 26 of elongate tubular member 20, and applied to radially surround elongate exterior recess 26 of side wall 20-5 of elongate tubular member 20. Stated differently, the powder coating coupled to the outer surface 20-6 of elongate tubular member 20 may extend around an entirety of elongate exterior recess 26 of side wall 20-5 of elongate tubular member 20.

In the powder coating embodiment, the powder coating forming pleural access liner 14 is made of, or made to include, at least one of collagen, silk fibroin, polyethylene glycol, hydroxypropyl methylcellulose, dehydrated gelatin, and starch (or other polysaccharide), which swells when hydrated.

Referring again to FIGS. 5 and 6, in some embodiments, it may be desired to confirm a deployed location of pleural access liner 14, wherein the confirmation may be determined by imaging, e.g., X-ray imaging. Accordingly, optionally, pleural access liner 14 may include a marking material or feature, e.g., a radiopaque material 30. Radiopaque material 30 may be, for example, a radiopaque substance (e.g., a barium composition) or a metallic element (e.g., stainless steel element).

Figure 7:
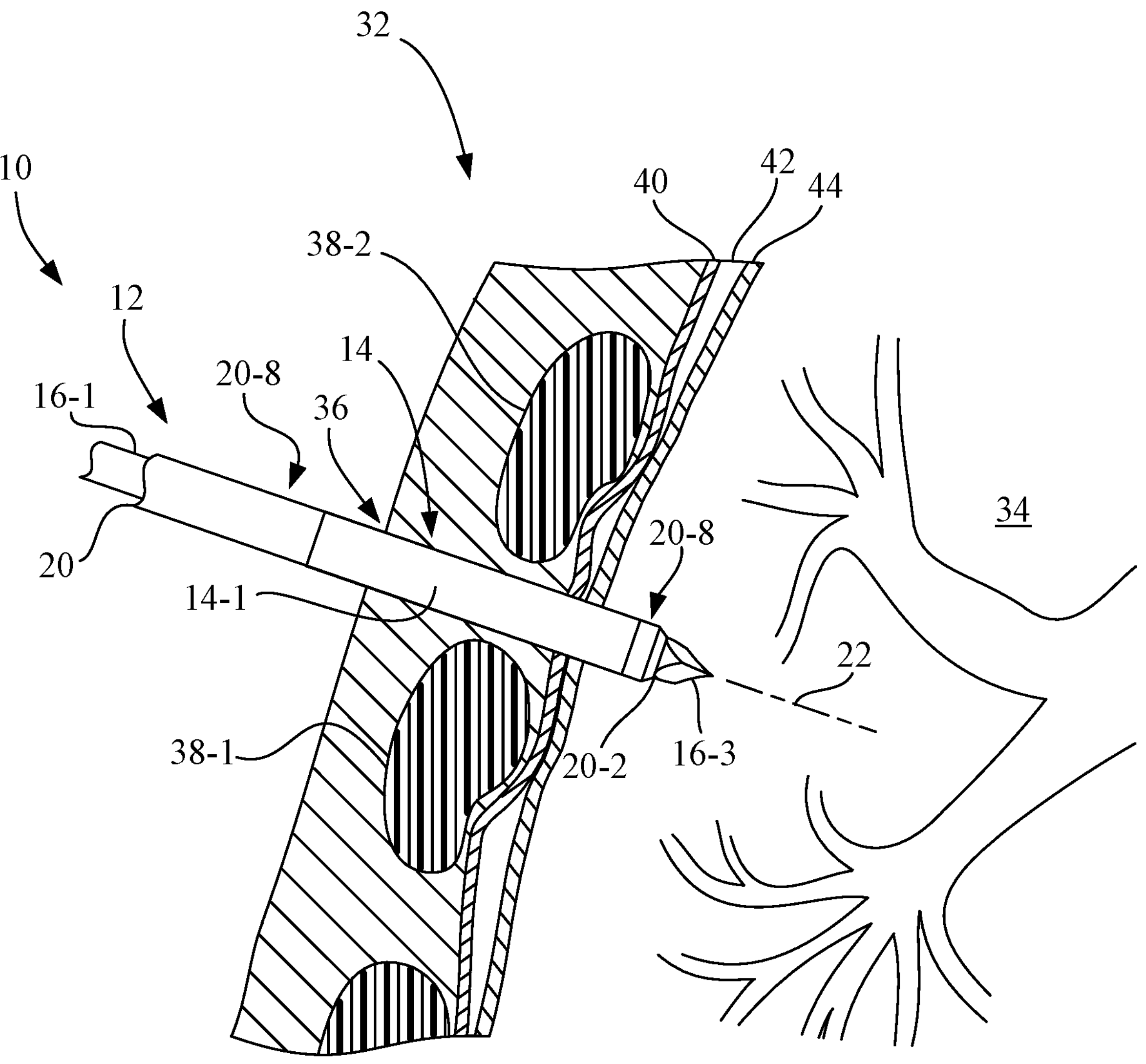
FIG. 7 is a pictorial representation of a portion of a chest wall and lung in cross-section, and with the introducer cannula, pleural access liner, and stylet of the pleural layers crossing system of FIGS. 1-6 positioned in an access opening in the chest wall and pleura layers of a patient.

FIG. 7 depicts a portion of a chest wall 32 and lung 34 of a patient, and shows pleural layers crossing system 10 having introducer cannula 12 and pleural access liner 14 in a deployed state, prior to hydration of pleural access liner 14. To achieve the deployed state depicted in FIG. 7, a stylet 16-1 is inserted through lumen 20-4 of introducer cannula 12 (see FIG. 3), with a piercing tip 16-3 of stylet 16-1 protruding from distal end 20-2 of elongate tubular member 20 of introducer cannula 12 (see FIGS. 1, 2, and 7).

Referring again to FIG. 7, stylet 16-1 in combination with introducer cannula 12 (carrying pleural access liner 14) are inserted into the patient to form an access opening 36 to the interior of lung 34. In particular, access opening 36 is formed between adjacent ribs 38-1, 38-2 in the rib cage of chest wall 32, and extends though the parietal pleura 40, the pleural space 42, and the visceral pleura 44 to provide access to the interior of lung 34. Once introducer cannula 12 and pleural access liner 14 enters into the lung parenchyma, it may be confirmed, e.g., through imaging, that pleural access liner 14 is positioned so as to cross parietal pleura 40, the pleural space 42, and the visceral pleura 44. Fluid in and around access opening 36 hydrates pleural access liner 14, such that pleural access liner 14 swells (see also FIG. 6) and seals the region between parietal pleura 40 and visceral pleura 44 along access opening 36, so as to aid in preventing pneumothorax.

A lung access procedure, such as a lung biopsy, may be carried out by removing stylet 16-1 from lumen 20-4 of elongate tubular member 20 of introducer cannula 12, and then inserting a lung biopsy device, e.g., a biopsy probe, through lumen 20-4 of elongate tubular member 20 of introducer cannula 12 and into the lung. At a conclusion of the lung access procedure, the lung biopsy device may be removed from elongate tubular member 20 of introducer cannula 12. Elongate tubular member 20 of introducer cannula 12 then may be removed from pleural access liner 14, such that pleural access liner 14 remains in access opening 36 to block air and fluid entry into pleural space 42, so as to aid in preventing pneumothorax. Upon removal of elongate tubular member 20 from pleural access liner 14, pleural access liner 14 may undergo further swelling to close elongate opening 14-2 of pleural access liner 14.

In some implementations, following the swelling of pleural access liner 14 during and following deployment, the coefficient of friction between pleural access liner 14 and access opening 36 of the patient may exceed the coefficient of friction between pleural access liner 14 and elongate tubular member 20 of introducer cannula 12, such that as elongate tubular member 20 of introducer cannula 12 is retracted from access opening 36, pleural access liner 14 remains in position in access opening 36.

Figure 8:
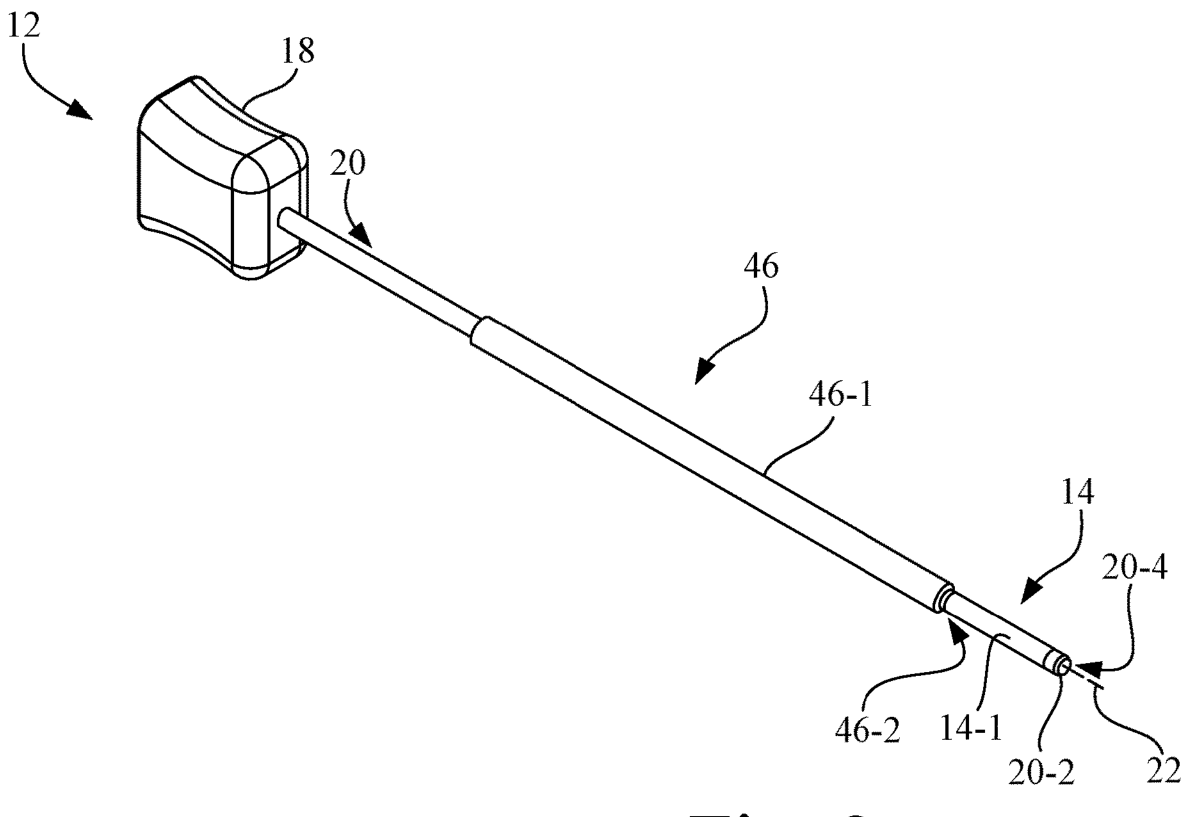
FIG. 8 is a perspective view of the introducer cannula that carries the pleural access liner, as show in FIG. 2, having a removal tool positioned between the handle body of the introducer cannula and the pleural access liner configured to aid in removal of the introducer cannula from the pleural access liner following deployment/hydration of the pleural access liner.
Figure 9:
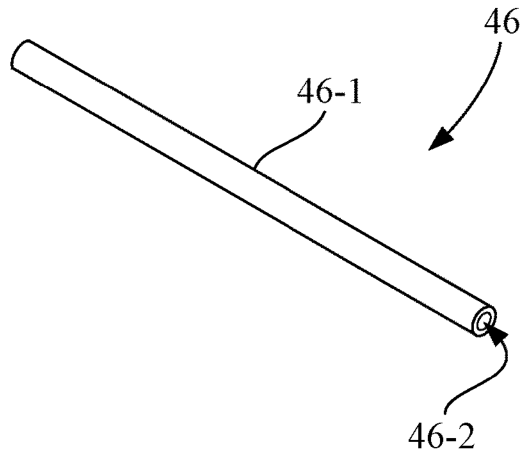
FIG. 9 is a perspective view of the pleural access liner removal tool of FIG. 8 in the absence of the introducer cannula.

However, it is contemplated that in some implementations, it may be desirable to provide a mechanical aid to assist in the removal of elongate tubular member 20 of introducer cannula 12 from pleural access liner 14. For example, with further reference to FIGS. 8 and 9, prior to deployment, a removal tool 46, e.g., in the form of an outer tube 46-1 having a lumen 46-2, may be positioned over elongate tubular member 20 at a location proximal to pleural access liner 14, e.g., between handle body 18 of introducer cannula 12 and elongate exterior recess 26 of elongate tubular member 20 that carries pleural access liner 14.

Following deployment and swelling of pleural access liner 14 in the patient, removal tool 46 may be slidably distally advanced into contact (if not already in contact) with pleural access liner 14 to aid in maintaining the position of pleural access liner 14 as elongate tubular member 20 is proximally withdrawn from removal tool 46 and pleural access liner 14. For example, removal tool 46 may be grasped by one hand of a user to maintain the fixed position of removal tool 46 in contact with pleural access liner 14, and the user may also grasp handle body 18 of introducer cannula 12 with the user's other hand. The user then pulls handle body 18 proximally to in turn proximally withdraw elongate tubular member 20 from removal tool 46 to leave pleural access liner 14 in its position in the access opening 36 of the patient. Thereafter, removal tool 46 may be removed from the patient and discarded.

The following items also relate to the invention:

In one form, the invention relates to an introducer cannula configured for crossing pleural layers/for use in crossing pleural layers. The introducer cannula may comprise an elongate tubular member and a pleural access liner. The elongate tubular member may have a proximal end, a distal end, and a side wall that longitudinally extends between the proximal end and the distal end, wherein the side wall has an outer surface and an inner surface, and wherein the inner surface defines a lumen. The pleural access liner may be made of a swellable and bioabsorbable material that is configured to swell when hydrated. The pleural access liner may have a shape of an elongate tube. The pleural access liner may have an optionally elongate opening that surrounds an outer surface portion of the outer surface of the elongate tubular member.

In some embodiments, the outer surface of the side wall of the elongate tubular member may have a first outer surface portion having a first diameter and a second outer surface portion having a second diameter that is less than the first diameter, wherein the second outer surface portion of the side wall defines an elongate exterior recess that extends around the elongate tubular member. The pleural access liner may reside in and surround the elongate exterior recess of the side wall of the elongate tubular member.

In any of the embodiments, the pleural access liner may be (initially, i.e. before use) a dehydrated material that radially extends around the outer surface of the elongate tubular member.

Optionally, in some embodiments, the pleural access liner may be an elongate cylindrical layer coupled to the outer surface of the elongate tubular member.

Optionally, in some embodiments, the pleural access liner may be a powder coating coupled to the outer surface of the elongate tubular member.

Optionally, the pleural access liner may be made of a polysaccharide.

Optionally, the pleural access liner may be made of at least one of collagen, silk fibroin, polyethylene glycol, hydroxypropyl methylcellulose, dehydrated gelatin, and starch.

Optionally, in some embodiments, the pleural access liner may be a pre-formed tube made of a foam material.

Optionally, in some embodiments, the pleural access liner may be a tube of woven or electrospun fibers.

Optionally, the pleural access liner may include a radiopaque material.

Optionally, the pleural access liner may be configured to be removed from the elongate tubular member.

In another form, the invention relates to an introducer cannula configured for crossing pleural layers/for use in crossing pleural layers, comprising an elongate tubular member and a bioabsorbable member. The elongate tubular member may have a proximal end, a distal end, and a side wall that longitudinally extends between the proximal end and the distal end, wherein the side wall has an inner surface that defines a lumen. The side wall may have a first outer surface portion having a first diameter and a second outer surface portion having a second diameter that is less than the first diameter, wherein the second outer surface portion of the side wall defines an elongate exterior recess of the side wall that extends around an entirety of the elongate tubular member. The bioabsorbable member may be positioned in the elongate exterior recess of the side wall of the tubular member. The bioabsorbable material may be configured to swell upon contact with a fluid.

In the embodiment of the preceding paragraph, the bioabsorbable member optionally may radially extend around an entirety of the elongate exterior recess of the side wall of the elongate tubular member.

Optionally, in some embodiments, the bioabsorbable member may be an elongate cylindrical layer coupled to the outer surface of the elongate tubular member and which extends around an entirety of the elongate exterior recess of the side wall of the elongate tubular member.

Optionally, in some embodiments, the bioabsorbable member may be a powder coating coupled to the outer surface of the elongate tubular member and which extends around an entirety of the elongate exterior recess of the side wall of the elongate tubular member.

Optionally, the bioabsorbable member may be made of a polysaccharide.

Optionally, the bioabsorbable member may be made of at least one of collagen, silk fibroin, polyethylene glycol, hydroxypropyl methylcellulose, dehydrated gelatin, and starch.

Optionally, in some embodiments, the bioabsorbable member may be a pre-formed tube made of a foam material.

Optionally, in some embodiments, the bioabsorbable member may be a tube of woven or electrospun fibers.

Optionally, the bioabsorbable member may include a radiopaque material.

Optionally, the bioabsorbable member may be configured to be removable from the elongate tubular member.

As used herein, "substantially," "generally," and other words of degree are relative modifiers intended to indicate permissible variation from the characteristic so modified. It is not intended to be limited to the absolute value or characteristic which it modifies but rather possessing more of the physical or functional characteristic than its opposite, and approaching or approximating such a physical or functional characteristic.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An introducer cannula for use in crossing pleural layers, comprising:

an elongate tubular member having a proximal end, a distal end, and a side wall that longitudinally extends between the proximal end and the distal end, the side wall having an outer surface and an inner surface, wherein the inner surface defines a lumen, wherein the outer surface of the side wall of the elongate tubular member has a first outer surface portion having a first diameter and a second outer surface portion that separates the first outer surface portion into two sections, the second outer surface portion having a second diameter that is less than the first diameter, wherein the second outer surface portion of the side wall defines an elongate exterior recess that extends around the elongate tubular member between the two sections of the first outer surface portion of the tubular member; and a pleural access liner made of a swellable and bioabsorbable material that swells when hydrated, wherein the pleural access liner has a shape of an elongate tube and the pleural access liner surrounds an outer surface portion of the outer surface of the elongate tubular member, wherein the pleural access liner resides in and surrounds the elongate exterior recess of the side wall of the elongate tubular member.

2. The introducer cannula according to claim 1, wherein a length of the elongate exterior recess is in a range of 2 to 5 centimeters.

3. The introducer cannula according to claim 1, wherein the pleural access liner is a dehydrated material that radially extends around the outer surface of the elongate tubular member.

4. The introducer cannula according to claim 1, wherein the pleural access liner is coupled to the outer surface of the elongate tubular member.

5. The introducer cannula according to claim 1, wherein the pleural access liner is a powder coating coupled to the outer surface of the elongate tubular member.

6. The introducer cannula according to claim 1, wherein the pleural access liner is made of a polysaccharide.

7. The introducer cannula according to claim 1, wherein the pleural access liner is made of at least one of collagen, silk fibroin, polyethylene glycol, hydroxypropyl methylcellulose, dehydrated gelatin, and starch.

8. The introducer cannula according to claim 1, wherein the pleural access liner is a pre-formed tube made of a foam material.

9. The introducer cannula according to claim 1, wherein the pleural access liner is a tube of woven or electrospun fibers.

10. The introducer cannula according to claim 1, wherein the pleural access liner includes a radiopaque material.

11. The introducer cannula according to claim 1, wherein the pleural access liner is configured to be removable from the elongate tubular member.

12. An introducer cannula for use in crossing pleural layers, comprising:

an elongate tubular member having a proximal end, a distal end, and a side wall that longitudinally extends between the proximal end and the distal end, the side wall having an inner surface that defines a lumen, the side wall having a first outer surface portion having a first diameter and a second outer surface portion that separates the first outer surface portion into two sections, the second outer surface portion having a second diameter that is less than the first diameter, wherein the second outer surface portion of the side wall defines an elongate exterior recess of the side wall that extends around an entirety of the elongate tubular member between the two sections of the first outer surface portion of the tubular member; and a bioabsorbable member positioned in the elongate exterior recess of the side wall of the tubular member, the bioabsorbable member constructed of a material that swells upon contact with a fluid.

13. The introducer cannula according to claim 12, wherein the bioabsorbable member radially extends around an entirety of the elongate exterior recess of the side wall of the elongate tubular member.

14. The introducer cannula according to claim 12, wherein the bioabsorbable member is an elongate cylindrical layer coupled to the outer surface of the elongate tubular member and which extends around an entirety of the elongate exterior recess of the side wall of the elongate tubular member.

15. The introducer cannula according to claim 12, wherein the bioabsorbable member is a powder coating coupled to the outer surface of the elongate tubular member and which extends around an entirety of the elongate exterior recess of the side wall of the elongate tubular member.

16. The introducer cannula according to claim 12, wherein the bioabsorbable member is made of a polysaccharide.

17. The introducer cannula according to claim 12, wherein the bioabsorbable member is made of at least one of collagen, silk fibroin, polyethylene glycol, hydroxypropyl methylcellulose, dehydrated gelatin, and starch.

18. The introducer cannula according to claim 12, wherein the bioabsorbable member is a pre-formed tube made of a foam material.

19. The introducer cannula according to claim 12, wherein the bioabsorbable member is a tube of woven or electrospun fibers.

20. The introducer cannula according to claim 12, wherein the bioabsorbable member includes a radiopaque material.

* * * * *